US008735389B2

(12) United States Patent
Seed et al.

(10) Patent No.: US 8,735,389 B2
(45) Date of Patent: *May 27, 2014

(54) TREATING PSYCHOLOGICAL CONDITIONS USING MUSCARINIC RECEPTOR $M_1$ ANTAGONISTS

(75) Inventors: Brian Seed, Boston, MA (US); Jordan Mechanic, Sunnyvale, CA (US)

(73) Assignee: Theracos, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/004,837

(22) Filed: Jan. 11, 2011

(65) Prior Publication Data

US 2011/0195952 A1     Aug. 11, 2011

Related U.S. Application Data

(63) Continuation of application No. 11/763,145, filed on Jun. 14, 2007, now Pat. No. 7,893,053.

(60) Provisional application No. 60/805,066, filed on Jun. 16, 2006, provisional application No. 60/829,225, filed on Oct. 12, 2006.

(51) Int. Cl.
| | | |
|---|---|---|
| *A01N 43/62* | (2006.01) | |
| *A61K 31/55* | (2006.01) | |
| *A61K 31/4965* | (2006.01) | |
| *A01N 43/54* | (2006.01) | |
| *A01N 47/28* | (2006.01) | |

(52) U.S. Cl.
USPC ....... 514/220; 514/255.01; 514/256; 514/580

(58) Field of Classification Search
USPC ........................................................ 514/220
See application file for complete search history.

(56) References Cited

U.S. PATENT DOCUMENTS

| | | |
|---|---|---|
| 3,953,430 A | 4/1976 | Safir |
| 4,536,518 A | 8/1985 | Welch, Jr. et al. |
| 4,839,104 A | 6/1989 | Quallich et al. |
| 4,940,731 A | 7/1990 | Bick |
| 4,962,128 A | 10/1990 | Doogan et al. |
| 5,114,976 A | 5/1992 | Norden |
| 5,130,338 A | 7/1992 | Bacopoulos |
| 5,248,699 A | 9/1993 | Sysko et al. |
| 5,442,116 A | 8/1995 | Welch et al. |
| 5,597,826 A | 1/1997 | Howard et al. |
| 5,744,501 A | 4/1998 | Norden |
| 5,789,449 A | 8/1998 | Norden |
| 6,034,274 A | 3/2000 | Vukics et al. |
| 6,517,866 B1 | 2/2003 | Am Ende et al. |
| 6,727,283 B2 | 4/2004 | Harper et al. |
| 7,067,555 B2 | 6/2006 | Harper et al. |
| 2004/0082653 A1 | 4/2004 | Nonaka et al. |
| 2005/0227998 A1 | 10/2005 | Voelker |

FOREIGN PATENT DOCUMENTS

| | | |
|---|---|---|
| CN | 101472571 B | 11/2012 |
| JP | 2009-530697 | 12/2009 |
| WO | 99/13877 A1 | 3/1999 |
| WO | 99/43647 A1 | 9/1999 |
| WO | 00/10551 A2 | 3/2000 |
| WO | 2006/017614 | 2/2006 |
| WO | WO 2006/113485 A2 | 10/2006 |
| WO | WO 2006/113485 A3 | 10/2006 |
| WO | WO 2006/127418 A1 | 11/2006 |
| WO | 2007/147123 | 12/2007 |

OTHER PUBLICATIONS

Lind et al., "Muscarinic acetylcholine receptor antagonists inhibit chick scleral chondrocytes," *Investigative Ophthalmology & Visual Science*, Nov. 1998, vol. 39, pp. 2217-2231.
Supplementary European Search Report mailed on Oct. 15, 2009, for EP Application No. 07784456.1, 3 pages.
Bechtel, W.D., et al., "Biochemical pharmacology of pirenzepine. Similarities with tricyclic antidepressants in antimuscarinic effects only," *Arzneimittelforschung*, vol. 36(5), pp. 793-796 (May 1986).
Chau, D.T., et al., "Nucleus accumbens muscarinic receptors in the control of behavioral depression: antidepressant-like effects of local $M_1$ antagonist in the Porsolt swim test," *Neuroscience*, vol. 104(3), pp. 791-798 (Jun. 2001).
Crowley et al., "Automated Tests for Measuring the Effects of Antidepressants in Mice," *Pharmacology, Biochemistry and Behavior*, 78 (2004) 269-274.
Cryan et al., "The Tail Suspension Test as a Model for Assessing Antidepressant Activity: Review of Pharmacological and Genetic Studies in Mice," *Neurosciences and Biobehavioral Reviews*, 29 (2005) 571-625.
Hammer, R., et al., "The pharmacokinetic profile of pirenzepine," *Scand. J. Gastroenterol. Suppl.*, vol. 57, pp. 1-6 (1979).
Ichikawa, J., et al., "Cholinergic modulation of basal and amphetamine-induced dopamine release in rat medial prefrontal cortex and nucleus accumbens," *Brain Research*, vol. 958, pp. 176-184 (2002).
Miyakawa, T., et al., "Hyperactivity and intact hippocampus-dependent learning in mice lacking the $M_1$ muscarinic acetylcholine receptor," *The Journal of Neuroscience*, 21(14), pp. 5239-5250 (Jul. 2001).
Rogóż, Z, et al., "Central Action of Pirenzepine," *Pol. Pharmacol. Pharm.*, vol. 33, pp. 615-626 (1981).
Steru et al., "The Tail Suspension Test: A New Method for Screening Antidepressants in Mice," *Psychopharmacology* (1985) 85: 367-370.
Trummlitz, G., et al., "Conformational analysis of the antiulcer drug pirenzepine. X-ray investigations, molecular mechanics and quantum mechanical calculations and comparisons with structurally or pharmacologically relatedcompounds," *Arzneimittelforschung*, vol. 34(8), pp. 849-859 (1984).

(Continued)

*Primary Examiner* — Layla Soroush
(74) *Attorney, Agent, or Firm* — Kilpatrick Townsend & Stockton LLP

(57) ABSTRACT

Provided are methods of treating psychological diseases and conditions by administration of a preferential muscarinic acetylcholine receptor $M_1$ antagonist, optionally with at least one antidepressant other than a selective muscarinic acetylcholine receptor $M_1$ antagonist. The invention also provides for pharmaceutical compositions and kits for administration of at least one selective muscarinic acetylcholine receptor $M_1$ antagonist in combination with at least one antidepressant other than a selective muscarinic acetylcholine receptor $M_1$ antagonist.

13 Claims, 6 Drawing Sheets

(56) References Cited

OTHER PUBLICATIONS

Gillin et al., "No antidepressant effect of biperiden compared with placebo in depression: A double-blind 6-week clinical trial," Psychiatry Research, 1995, vol. 58, pp. 99-105.

Kasper et al., "The Anticholinergic Biperiden in Depressive Disorders," Pharmacopsychiatria, 1981, vol. 14, No. 6, pp. 195-198.

Gouret et at "Biochemical and pharmacological evaluation of the novel antidepressant and serotonin uptake inhibitor 2-(3,4-Dicholoobenzyl)-2-dimethylamino-1-propanol hydrochloride," http://www.ncbi.nlm.nih.gov;pubmed/2168703, Institut de Recherche Jouveinal, Arzneimittelforschung, 1990, No. 40(6), abstract only.

Londong et al., "Telenzpine is at least 25 times more potent than pirenzepine—a dose response and comparative secretory study in man," Gut, 1987, vol. 28, pp. 888-895.

TREATING PSYCHOLOGICAL CONDITIONS USING MUSCARINIC RECEPTOR $M_1$ ANTAGONISTS

CROSS-REFERENCE TO RELATED APPLICATIONS

This application claims the benefit of U.S. Provisional Application No. 60/805,066, filed Jun. 16, 2006 and U.S. Provisional Application No. 60/829,225, filed Oct. 12, 2006, the entire disclosures of both of which are hereby incorporated herein by reference.

STATEMENT AS TO RIGHTS TO INVENTIONS MADE UNDER FEDERALLY SPONSORED RESEARCH AND DEVELOPMENT

Not Applicable

FIELD OF THE INVENTION

The present invention relates to the treatment of psychological disorders, including depression, by administration of a selective $M_1$ muscarinic receptor ($M_1R$) antagonist, alone or in combination with an antidepressant.

BACKGROUND OF THE INVENTION

The neurotransmitter acetylcholine (ACh) interacts with two types of receptors in effector cell membranes: nicotinic receptors (nAChR), which are ligand-gated ion channels, and muscarinic receptors (mAChR), which are G protein-coupled receptors. In mammals five subtypes of mAChR, designated $M_1$ to $M_5$, have been identified. The $M_1$ muscarinic receptor ($M_1R$) is found in both the central and peripheral nervous systems, particularly the cerebral cortex and sympathetic ganglia. The muscarinic effects mediated by $M_1R$ have been studied largely by use of $M_1R$-selective antagonists and, more recently, by the development of $M_1R$-null mice.

Although no currently known mAChR antagonists display absolute selectivity for a single muscarinic receptor subtype, the drugs pirenzepine and telenzepine exhibit high relative affinity for $M_1R$ and are therefore often considered $M_1R$-selective. Pirenzepine is used to treat peptic ulcer disease in Europe, Japan and Canada. Telenzepine has been tested in clinical trials for the same indication. At therapeutic doses, they moderately reduce gastric acid and pepsin secretion without inhibiting smooth muscle activity as do non-selective mAChR antagonists.

There are several lines of evidence suggesting that the $M_1R$ subtype may be involved in certain aspects of depressive disorders and anxiety. Direct injection of pirenzepine into the nucleus accumbens in the forebrain of rats resulted in increased swimming time in the Porsolt swim test (see, Chau, D. T., et al., *Neuroscience*, 2001, vol. 104, no. 3, pp. 791-8), a common measure of antidepressant activity. $M_1R$-null mice also displayed increased swimming time in the Porsolt swim test, as well as increased social contacts in a social interaction test (see, Miyakawa, T., et al., *J. Neurosci.*, 2001, vol. 21, no. 14, pp. 5239-50).

While pirenzepine and telenzepine are structurally similar to tricyclic antidepressants such as imipramine, they are not known to have psychotropic effects when taken orally for the treatment of peptic ulcer disease. In addition, in earlier studies of mice and rats, pirenzepine administered systemically failed to elicit any behavioral effects (see, Rogoz, Z., Skuza, G., Sowinska, H., *Pol. J. Pharmacol. Pharm.*, 1981, vol. 31, pp. 615-26). The lack of such effects can be explained by the observation that pirenzepine does not exhibit significant penetration of the blood-brain barrier in various species, including rodents and humans (see, Hammer, R., Koss, F. W., *Scand. J. Gastroenterol., Suppl.*, 1979, vol. 14, no. 57, pp. 1-6; Bymaster, F. P., et al., *J. Pharmacol. Exp. Ther.*, 1993, vol. 267, no. 1, pp. 16-24). It is for that reason that the above-mentioned study of the effect of pirenzepine in the Porsolt swim test utilized direct injection of the drug into the brain of test animals.

There exists a need for new and effective medications for the treatment of psychological conditions, including depression. The present invention addresses this and other needs.

BRIEF SUMMARY OF THE INVENTION

The present invention provides methods for treating various psychological disorders, including depression, by systemically administering a therapeutically effective amount of one or more muscarinic M1 receptor ($M_1R$-selective) antagonists. In practicing the present methods, the one or more $M_1R$-selective antagonists can be administered without other pharmacological agents or in combination with other pharmacological agents, for example, one or more antidepressants other than a $M_1R$-selective antagonist.

Accordingly, in a first aspect, the present invention provides methods for treating one or more psychological conditions or disorders by systemically administering to an individual in need thereof a therapeutically effective amount of one or more selective $M_1R$-selective antagonists, whereby the one or more psychological conditions are treated.

In a related aspect, the invention provides methods for treating one or more psychological conditions or disorders by administering to an individual in need thereof a therapeutically effective amount of a combination of one or more $M_1R$-selective antagonists and one or more antidepressants other than a $M_1R$-selective antagonist, whereby the one or more psychological conditions are treated.

In one embodiment, the psychological disorder is an affective disorder. In one embodiment, the psychological condition is depression. In one embodiment, the psychological condition is selected from the group consisting of depression, anxiety, social anxiety disorder, agoraphobia, obsessive-compulsive disorder, post-traumatic stress disorder, body dysmorphic disorder, premenstrual dysphoric disorder, and substance abuse and/or dependence.

In another aspect, the invention provides pharmaceutical compositions comprising a mixture of therapeutically effective amounts of one or more $M_1R$-selective antagonists and one or more antidepressants other than a $M_1R$-selective antagonist.

In another aspect, the invention provides kits comprising a mixture of therapeutically effective amounts of one or more $M_1R$-selective antagonists and one or more antidepressants other than a $M_1R$-selective antagonist.

With regard to the embodiments for carrying out the methods, and for the pharmaceutical compositions and kits, in one embodiment, the one or more $M_1R$-selective antagonists is selected from the group consisting of pirenzepine, telenzepine, and combinations thereof. In one embodiment, the $M_1R$-selective antagonist is telenzepine (racemic or an optical isomer). In one embodiment, the $M_1R$-selective antagonist is pirenzepine.

In one embodiment, the one or more $M_1R$-selective antagonists are administered without a second pharmacological agent.

In one embodiment, the one or more $M_1R$-selective antagonists is administered in combination with or combined with one or more antidepressants other than a $M_1R$-selective antagonist. In one embodiment, the antidepressant is selected from the group consisting of a selective serotonin reuptake inhibitor (SSRI) and a selective serotonin-norepinephrine reuptake inhibitor (SNRI).

In one embodiment, the antidepressant is a SSRI. In one embodiment, the SSRI is selected from the group consisting of citalopram, escitalopram, fluoxetine, fluvoxamine, paroxetine and sertraline. In one embodiment, the SSRI is selected from the group consisting of citalopram, sertraline, paroxetine, and fluoxetine.

In one embodiment, the antidepressant is a SNRI. In one embodiment, the SNRI is selected from the group consisting of milnacipran, mirtazapine, venlafaxine, duloxetine, desvenlafaxine and sibutramine. In one embodiment, the SNRI is venlafaxine.

Efficacious results can be achieved without timed administration of the one or more $M_1R$-selective antagonists. Co-administered active agents, including antidepressants, also provide efficacious results without timed administration.

In one embodiment, the one or more $M_1R$-selective antagonists is telenzepine (racemic or an optical isomer) and the one or more antidepressants other than a $M_1R$-selective antagonist is fluoxetine (racemic or an optical isomer).

In one embodiment, the one or more $M_1R$-selective antagonists is telenzepine (racemic or an optical isomer) and the one or more antidepressants other than a $M_1R$-selective antagonist is fluvoxamine.

In one embodiment, the one or more $M_1R$-selective antagonists is telenzepine (racemic or an optical isomer) and the one or more antidepressants other than a $M_1R$-selective antagonist is sertraline or its S-enantiomer, Zoloft®.

In one embodiment, the one or more $M_1R$-selective antagonists is telenzepine (racemic or an optical isomer) and the one or more antidepressants other than a $M_1R$-selective antagonist is citalopram (or escitalopram).

In one embodiment, the one or more $M_1R$-selective antagonists is telenzepine (racemic or an optical isomer) and the one or more antidepressants other than a $M_1R$-selective antagonist is paroxetine.

In one embodiment, the one or more $M_1R$-selective antagonists is telenzepine (racemic or an optical isomer) and the one or more antidepressants other than a $M_1R$-selective antagonist is venlafaxine (racemic or an optical isomer).

In one embodiment; the one or more $M_1R$-selective antagonists is telenzepine (racemic or an optical isomer) and the one or more antidepressants other than a $M_1R$-selective antagonist is desvenlafaxine.

In one embodiment, the one or more $M_1R$-selective antagonists is telenzepine (racemic or an optical isomer) and the one or more antidepressants other than a $M_1R$-selective antagonist is duloxetine.

In one embodiment, the one or more $M_1R$-selective antagonists is telenzepine (racemic or an optical isomer) and the one or more antidepressants other than a $M_1R$-selective antagonist is sibutramine.

In one embodiment, the one or more $M_1R$-selective antagonists is telenzepine (racemic or an optical isomer) and the one or more antidepressants other than a $M_1R$-selective antagonist is milnacipran.

In one embodiment, the one or more $M_1R$-selective antagonists is telenzepine (racemic or an optical isomer) and the one or more antidepressants other than a $M_1R$-selective antagonist is mirtazapine.

In one embodiment, the one or more $M_1R$-selective antagonists is telenzepine (racemic or an optical isomer) and the one or more antidepressants other than a $M_1R$-selective antagonist is bupropion.

In a related aspect, the invention provides methods for preparing or use of a medicament for treating one or more psychological conditions, the medicament containing a therapeutically effective amount of one or more $M_1R$-selective antagonists. The medicament can optionally also contain one or more antidepressants other than a $M_1R$-selective antagonist. The embodiments for the medicament are as described herein.

In some embodiments, the methods and compositions of the invention comprise the combinations of pharmacological agents set forth herein. In some embodiments, the methods and compositions of the invention consist essentially of the combinations of pharmacological agents set forth herein.

DEFINITIONS

The term "psychological disorder" or "psychological condition" interchangeably refer to a disorder of thought or emotion or a disorder of the brain that results in a disruption in a person's thinking, feeling, moods, and ability to relate to others. A psychological disorder or condition can manifest as inappropriate or unprovoked expressions of anger, sadness, fear, anxiety, or other sociopathic behaviors, for example. Exemplified categories of psychological disorders include, without limitation, affective disorders, anxiety disorders, cognitive disorders, impulse control disorders, substance abuse/dependence disorders, attention deficit/hyperactivity disorders, eating disorders, movement disorders and sexual dysfunctions. Exemplified psychological conditions treatable by the present methods and compositions include, without limitation, depression, anxiety, social anxiety disorder, agoraphobia, obsessive-compulsive disorder, post-traumatic stress disorder, body dysmorphic disorder, premenstrual dysphoric disorder and substance abuse/dependence. Psychological disorders are described, for example, in Halgin and Whitbourne, *Abnormal Psychology: Clinical Perspectives On Psychological Disorders,* 4th Edition, 2005, McGraw-Hill College; Barlow and Antony, *Handbook of Assessment and Treatment Planning for Psychological Disorders,* 2002, Guilford Press; Claridge and Davis, *Personality and Psychological Disorders,* 2003, Oxford Univ Pr; and *Clinical Handbook of Psychological Disorders: A Step-by-Step Treatment Manual,* Barlow, Ed., 2001, Guilford Press. Diagnostic criteria for recognized psychological disorders can be made with reference to *Diagnostic and Statistical Manual of Mental Disorders* (DSM IV, 2000, American Psychiatric Association).

The term "affective disorder" refers to any disorder of mood. Affective disorders include depression, mania, bipolar disorder, seasonal affective disorder, anxiety, panic. See, for example, Paykel, *Handbook of Affective Disorders,* 1992, Longman Group Ltd.

The term "depression" refers to a clinical syndrome consistent with its accepted meaning in the art (see, for example, *Diagnostic and Statistical Manual of Mental Disorders,* Fourth Edition, Text Revision [DSM-IV-TR]; American Psychiatric Association, 2000; American Psychiatric Publishing, Inc., Arlington, Va.). Symptoms of depression include, but are not limited to, persistent sadness, feelings of pessimism, despair, feelings of helplessness, feelings of worthlessness, changes in moods, agitation, irritability, restlessness, loss of interest or pleasure in activities once enjoyed, thoughts of death or suicide, inability to concentrate or make decisions, mental slowness, fatigue, decreased energy, insomnia or oversleeping, loss of appetite or overeating, weight loss or weight gain, persistent headaches or digestive disorders, chronic pain, and abnormal hormonal circadian rhythms.

The term "substance dependence" is used in accordance with its commonly understood meaning by those of skill in the art. For example, a clinical diagnosis of "substance dependence" according to the International Classification of Diseases requires that three or more of the following must have been experienced or exhibited by the individual at some time during the previous year: (1) difficulties in controlling substance-taking behavior in terms of its onset, termination, or levels of use; (2) a strong desire or sense of compulsion to take the substance; (3) progressive neglect of alternative pleasures or interests because of psychoactive substance use, increased amount of time necessary to obtain or take the substance or to recover from its effects; (4) persisting with substance use despite clear evidence of overtly harmful consequences, depressive mood states consequent to heavy use, or drug related impairment of cognitive functioning; (5) evidence of tolerance, such that increased doses of the psychoactive substance are required in order to achieve effects originally produced by lower doses; (6) a physiological withdrawal state when substance use has ceased or been reduced, as evidence by: the characteristic withdrawal syndrome for the substance; or use of the same (or a closely related) substance with the intention of relieving or avoiding withdrawal symptoms. Further information regarding substance abuse can be found, for example, on the website for the National Institute on Drug Abuse (NIDA) at nida.nih.gov.

As used herein, "administering" means oral ("po") administration, administration as a suppository, topical contact, intravenous ("iv"), intraperitoneal ("ip"), intramuscular ("im"), intralesional, intranasal or subcutaneous ("sc") administration, or the implantation of a slow-release device e.g., a mini-osmotic pump, to a subject. Administration is by any route including parenteral and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intraarterial, transdermal and subcutaneous) administration, with the proviso that, as used herein, systemic administration does not include direct administration to the brain region by means other than via the circulatory system, such as intrathecal injection and intracranial administration.

The term "co-administer" refers to the simultaneous presence of two active agents in the blood of an individual. Active agents that are co-administered can be concurrently or sequentially delivered.

As used herein, the terms "treating" and "treatment" refer to delaying the onset of, retarding or reversing the progress of, or alleviating or preventing either the disease or condition to which the term applies, or one or more symptoms of such disease or condition.

As used herein, the terms "selective muscarinic receptor $M_1$ antagonist" and "$M_1$R-selective antagonist" refer to a muscarinic acetylcholine receptor antagonist that exhibits preferential interaction with the muscarinic receptor $M_1$ subtype in comparison to the muscarinic receptor subtypes $M_2$ and $M_3$. Exemplified $M_1$R-selective antagonists include, but are not limited to, pirenzepine and telenzepine. Preferential binding need not be complete. For example, despite comparable affinities for $M_1$ and $M_4$ receptor subtypes, pirenzepine is classified as an $M_1$R-selective antagonist.

Preferential binding of a $M_1$R-selective antagonist can be measured in a competitive displacement assay. A $M_1$R-selective antagonist will preferentially displace a known $M_1$R-selective ligand (e.g., pirenzepine and/or telenzepine) in comparison to known $M_2$ (e.g., tripitramine, himbacine, methoctramine) and $M_3$ (e.g., darifenacin, hexahydrosiladiphenidol) selective ligands. Alternatively, a $M_1$R-selective antagonist will preferentially displace a nonselective muscarinic ligand (e.g., quinuclidinyl benzilate (QNB), N-methylscopolamine (NMS)) from an $M_1$ receptor subtype in comparison to displacing the non-selective muscarinic ligand from binding to the $M_2$ and $M_3$ receptor subtypes. The relative potencies for displacement of radiolabeled competitors can be expressed in terms of the concentration at which 50% of the competitor is displaced ($IC_{50}$), or in terms of an equilibrium dissociation constant ($K_d$). The $IC_{50}$ value and/or the equilibrium dissociation constant can be calculated using available software by entering the values of detected labeled ligand in the presence of titrated amounts of unlabeled test compound (e.g., LIGAND (Munson, P. J., and Rodbard, D., *Anal. Biochem.* (1980) 107:220-39 or DATAPLOT, National Technical Information Services). A $M_1$R-selective antagonist will have an $IC_{50}$ value or a $K_d$ value for binding to an $M_1$ receptor subtype that is at least about 3-fold less, preferably at least about 10-fold less, and more preferably at least about 30-fold less than its $IC_{50}$ value or $K_d$ value for binding to $M_2$ and $M_3$ receptor subtypes. Applicable radioligand binding assays, using radiolabeled NMS or QNB, are disclosed in Buckley, et al., *Molecular Pharmacology* (1989) 35:469-76 and Bolden, et al, *J Pharmacol Exp Ther*. (1992) 260:576-80.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than a $M_1$R-selective antagonist and an antidepressant. In some embodiments, additional active agents that can be excluded include one or more of a prolactin inhibitor, a prolactin stimulator, a 5-HT receptor antagonist, a 5-HT receptor agonist, a NK-1 receptor antagonist and/or a dipeptidylpeptidase IV inhibitor.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in *Remington: The Science and Practice of Pharmacy*, 21$^{st}$ Ed., Lippencott Williams & Wilkins (2006). As discussed therein, immediate and nonimmediate release can be defined kinetically by reference to the following equation:

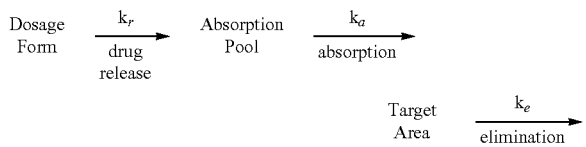

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area.

The terms "sustained release" and "extended release" are used in their conventional sense to refer to a drug formulation that provides for gradual release of a drug over an extended period of time, for example, 12 hours or more, and that preferably, although not necessarily, results in substantially steady-state blood levels of a drug over an extended time period.

As used herein, the term "delayed release" refers to a pharmaceutical preparation that passes through the stomach intact and dissolves in the small intestine.

As used herein, "synergy" or "synergistic" interchangeably refer to the combined effects of two active agents that are greater than their additive effects. Synergy can also be achieved by producing an efficacious effect with combined inefficacious doses of two active agents. The measure of synergy is independent of statistical significance.

DETAILED DESCRIPTION

1. Introduction

Figure 1:
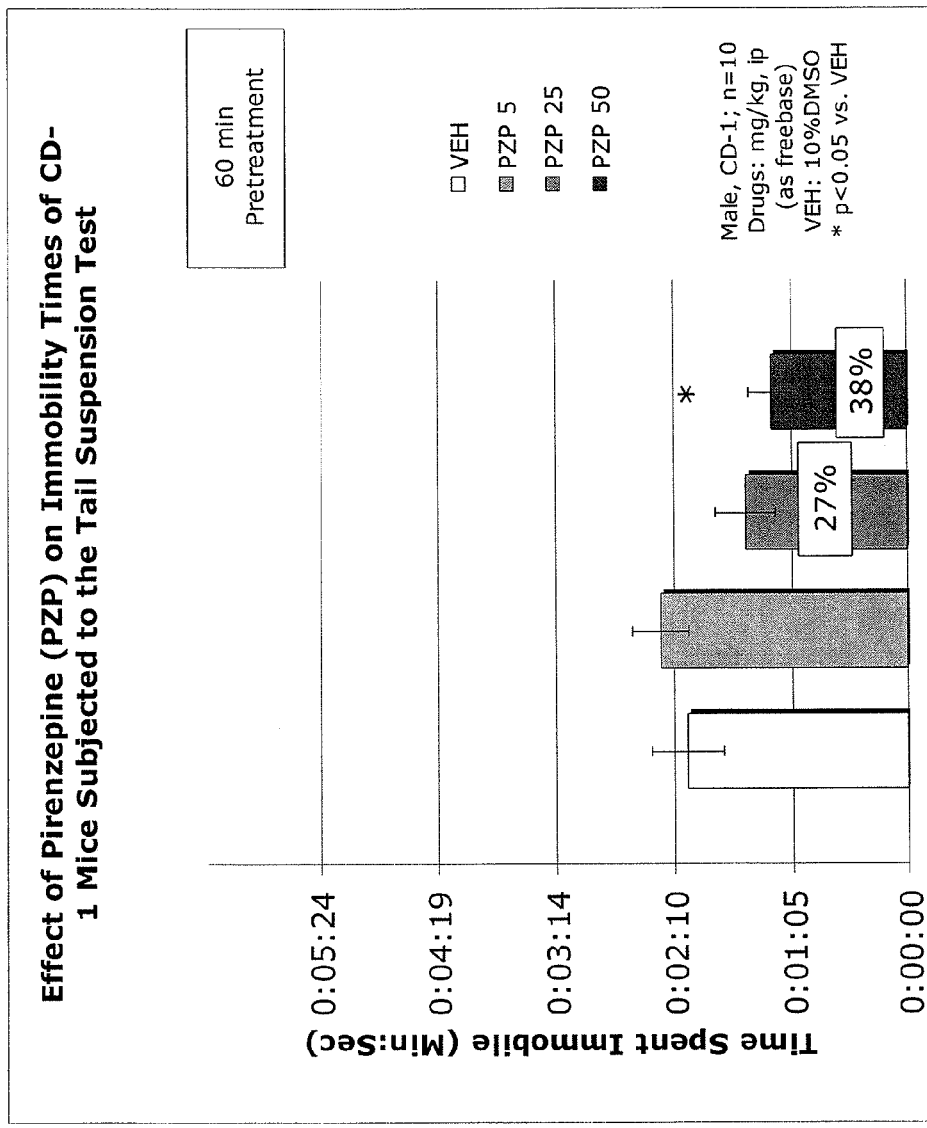
FIG. 1 illustrates the effect of pirenzepine (PZP) administered intraperitoneally on immobility times of CD-1 mice subjected to the tail suspension test. Male CD-1 mice (n=10 per group) were administered pirenzepine as free base in doses of 5 mg/kg, 25 mg/kg or 50 mg/kg as described in the Examples below. Control mice (VEH) were administered 10% DMSO. * indicates p<0.05 vs. VEH.
Figure 2:
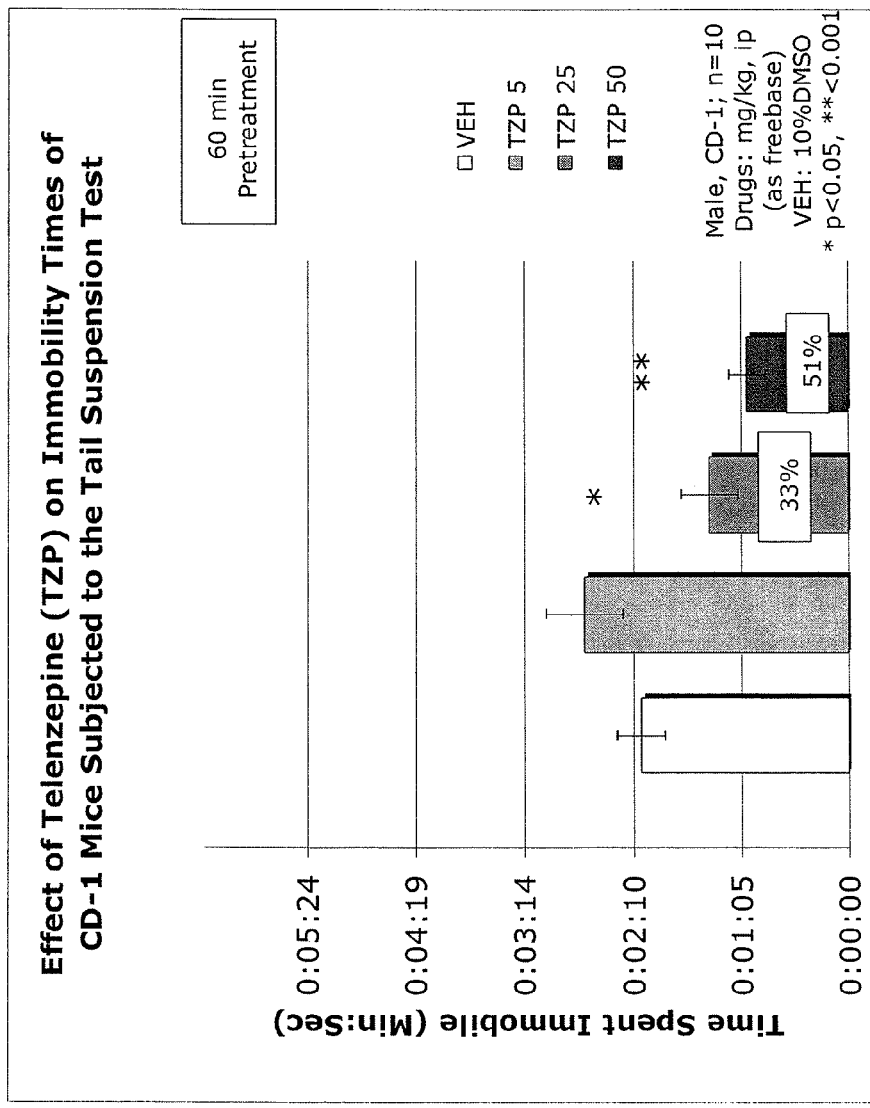
FIG. 2 illustrates the effect of telenzepine (TZP) administered intraperitoneally on immobility times of CD-1 mice subjected to the tail suspension test. Male CD-1 mice (n=10 per group) were administered telenzepine as free base in doses of 5 mg/kg, 25 mg/kg or 50 mg/kg as described in the Examples below. Control mice (VEH) were administered 10% DMSO. * indicates p<0.05 vs. VEH. ** indicates p<0.001 vs. VEH.
Figure 3:
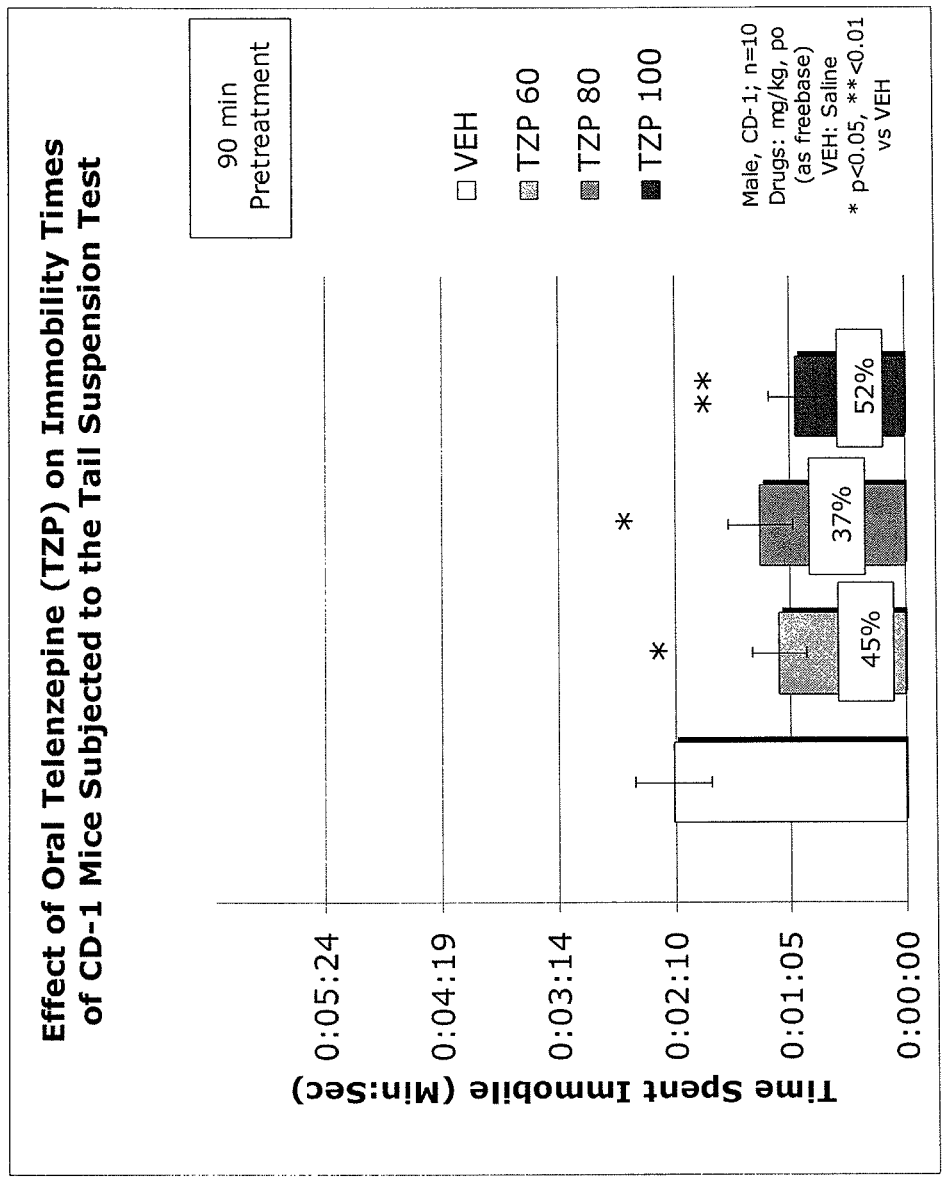
FIG. 3 illustrates the effect of oral telenzepine (TZP) on immobility times of CD-1 mice subjected to the tail suspension test. Male CD-1 mice (n=10 per group) were administered telenzepine as free base in doses of 60 mg/kg, 80 mg/kg or 100 mg/kg as described in the Examples below. Control mice (VEH) were administered saline. * indicates p<0.05 vs. VEH. ** indicates p<0.01 vs. VEH.

As discussed above, earlier studies in rats and mice demonstrated that pirenzepine administered systemically failed to elicit any behavioral effects (see, Rogoz, Z., Skuza, G., Sowinska, H., *Pol. J. Pharmacol. Pharm.*, 1981, vol. 31, pp. 615-26), and that pirenzepine does not exhibit significant penetration of the blood-brain barrier in various species, including rodents and humans (see, Hammer, R., Koss, F. W., Scand. *J. Gastroenterol., Suppl.*, 1979, vol. 14, no. 57, pp. 1-6; Bymaster, F. P., et al., *J. Pharmacol. Exp. Ther.*, 1993, vol. 267, no. 1, pp. 16-24). Surprisingly, contrary to the published literature, the current invention demonstrates that $M_1R$-selective antagonists, including pirenzepine and telenzepine, can cross the blood-brain barrier in therapeutic amounts and therefore have useful antidepressant activity when administered systemically. These agents also are useful for treating other psychological conditions often treated with antidepressants.

The present invention also demonstrates that the use of $M_1R$-selective antagonists in combination with certain other therapeutic agents produces unexpected synergistic effects that are advantageous for treating psychological conditions, including depression.

The present invention provides an efficacious pharmacological treatment for depression, anxiety, social anxiety disorder, agoraphobia, obsessive-compulsive disorder, post-traumatic stress disorder, body dysmorphic disorder, premenstrual dysphoric disorder and substance abuse or dependence (e.g., nicotine, alcohol, sedatives, etc.). Systemic administration of a selective muscarinic receptor $M_1$ ($M_1R$-selective) antagonist unexpectedly provides antidepressant effects. Surprisingly, therapeutically effective amounts of one or more $M_1R$-selective antagonists efficacious in treating psychological disorders, including depression, can cross the blood-brain barrier when systemically administered to a subject. In addition, co-administration of one or more $M_1R$-selective antagonists and one or more antidepressant agents other than a $M_1R$-selective antagonist unexpectedly provides for greater antidepressant effects than is accomplished by administering any of these categories of drug alone.

2. Methods of Treating Psychological Disorders a. Conditions Subject to Treatment The present methods and compositions find use in the treatment of psychological disorders. Exemplified general categories of psychological disorders treatable by the present methods and compositions include, without limitation, (1) affective, anxiety and impulse control disorders (including pathological overeating), (2) substance abuse/dependence disorders (i.e., addictive behaviors), (3) cognitive, attention deficit and hyperactivity disorders, (4) movement disorders and sexual dysfunctions, and (5) eating disorders (e.g., anorexia nervosa and bulimia nervosa).

The action of acetylcholine on muscarinic receptors in the central nervous system influences a diverse array of behaviors, including cognition, insight, vigilance, affect, sensory-motor gating and both reflexive and directed motility (Bymaster et al., *Curr Drug Targets CNS Neurol Disord* (2002) 1:163-181). Muscarinic receptors influence these functions not only through interactions with cholinergic neurons, but also through modulation of the activity of forebrain/midbrain dopaminergic, GABAergic and glutamatergic neurons. Neurolocalization and microdialysis studies have confirmed the influence muscarinic receptors and their agonists or antagonists have over these systems, with the directionality of modulation (excitation/inhibition) dependent on the specific receptor subtype. Specifically, local microinjection of the $M_1/M_4$ preferring antagonist, pirenzepine, results in decreased dopamine efflux in the striatum (Smolders et al., *J Neurochem* (1997) 68:1942-1948). Similarly, when directly injected into the midbrain, the $M_1/M_4$ receptor preferring antagonist, telenzepine, produces reduced GABA efflux (Smolders et al., 1997, supra). Likewise, non-subtype selective antagonists, such as scopolamine, produce elevated acetylcholine levels in the forebrain (Izurieta-Sanchez et al., *Eur J Pharmacol* (2000) 399:151-160).

With regard to substance abuse and disorders of dependence, mesolimbic dopamine circuits are thought to play important roles in the formation and perpetuation of addictive behavior (Berridge and Robinson, *Brain Res Brain Res Rev* (1998) 28:309-369; Crespo et al., *J Neurosci* (2006) 26:6004-6010; Di Chiara and Imperato, *Proc Natl Acad Sci USA* (1988) 85:5274-5278; Hernandez and Hoebel, *Life Sci* (1988) 42:1705-1712). Studies with rodents have shown that a specific structure in the striatum, the nucleus accumbens (NAc), is involved in the regulation of reward and aversion. The NAc lies in the medioventral striatum and can be further dissected into shell, core and rostral pole subterritories (Zahm and Brog, *Neuroscience* (1992) 50:751-767).

Rats will self-administer dopamine agonists into the NAc (Hoebel et al., *Psychopharmacology (Berl)* (1983) 81:158-163) and a large number of drugs that are known to provoke abuse and habituation in humans have been shown to increase extracellular dopamine levels in the NAc (Di Chiara and Imperato, 1988, supra; Hernandez and Hoebel, 1988, supra; Rada et al., *Pharmacol Biochem Behav* (1996) 53:809-816). Conversely, decreased extracellular dopamine in the nucleus accumbens has been observed to accompany aversion during morphine-induced and nicotine-induced withdrawal (Acquas and Di Chiara, (1992) *J Neurochem* 58:1620-1625; Diana et al., *J Pharmacol Exp Ther* (1995) 272:781-785; Pothos et al., *Brain Res* (1991) 566:348-350; Rada et al., *Psychopharmacology (Berl)* (2001) 157:105-110). The effects of dopamine appear to be mediated by receptor subtypes D1 and D2. Injection of dopamine D1 or D2 agonists into the NAc shell but not core, has been shown to reinstate drug-seeking behavior in rats that have been operantly conditioned to press levers for cocaine, but then have had the behavior extinguished by substituting saline for cocaine (Schmidt et al., *Eur J Neurosci* (2006) 23:219-228).

Within the NAc cholinergic and dopaminergic circuits appear to be pharmacologically opposed. Local intra-accumbal administration of either atropine (a nonspecific muscarinic antagonist) or mecamylamine (a nonspecific nicotinic antagonist) has been reported to block the acquisition of opiate reinforcement (Crespo et al., 2006, supra), whereas morphine decreases acetylcholine levels in the NAc (Fiserova et al., *Psychopharmacology (Berl)* (1999) 142:85-94; Rada et al., *Neuropharmacology* (1991) 30:1133-1136) and naloxone-induced opiate withdrawal increases acetylcholine levels (Fiserova et al., 1999, supra; Rada et al., 1991 supra; Rada et al., 1996, supra). Similar phenomena have been observed in conjunction with mecamylamine-induced withdrawal in nicotine-dependent rats (Rada et al., 2001, supra). In support of a broad general connection between elevated ACh and dysphoric states, ACh is released in the NAc by a conditioned aversive taste (Mark et al., *Brain Res* (1995) 688:184-188), aversive brain stimulation (Rada and Hoebel, *Brain Res* (2001) 888:60-65), and withdrawal from diazepam (Rada and Hoebel, *Eur J Pharmacol* (2005) 508:131-138), alcohol (Rada et al., *Pharmacol Biochem Behav* (2004) 79:599-605) or sugar (Colantuoni et al., *Obes Res* (2002) 10, 478-488). Attenuation of cholinergic transmission is thus a therapeutically attractive approach to the treatment of disorders of addiction and habituation. Such disorders need not be purely pharmacologic as the findings with sucrose withdrawal exemplify.

Accordingly, neuropsychiatric applications for compounds that possess the ability to preferentially modulate $M_1$ muscarinic receptors are widespread. Therefore, the present methods find use in treating a variety of conditions, including those resulting from impaired: i) cognitive processing, ii) affective processing, and/or iii) appetitive motivation. Conditions within these categories include (1) affective, anxiety and impulse control disorders (including pathological overeating), (2) substance abuse/dependence disorders (i.e., addictive behaviors), (3) cognitive, attention deficit and hyperactivity disorders, (4) movement disorders and sexual dysfunctions, and (5) eating disorders (e.g., anorexia nervosa and bulimia nervosa).

Exemplified affective, anxiety and impulse control disorders include affective disorders (including but not limited to depression, bipolar disorder, dysthymic disorder, premenstrual dysphoric disorder), anxiety disorders (including but not limited to generalized anxiety disorder, social anxiety disorder, panic disorder, post-traumatic stress disorder, obsessive compulsive disorder, agoraphobia, specific phobias, conversion disorders, body dysmorphic disorder), and impulse control disorders (including but not limited to kleptomania, pyromania, trichotillomania, pathological gambling, pathological overeating).

Exemplified substance abuse and/or dependence disorders include physical and/or psychological dependence on pharmacological agents, including but not limited to nicotine, alcohol, opioids, psychostimulants, sedatives/hypnotics. The term "opioids" includes, without limitation, natural, semisynthetic and unnatural agonists or partial agonists of opioid receptors. The term "psychostimulants" includes, without limitation, antagonists of the dopamine reuptake transporter and/or agents which directly promote dopamine release and comprise without limitation, cocaine, synthetic dopamine transporter inhibitors, amphetamines, phenmetrazine and methylenedioxyamphetamines.

Exemplified cognitive, attention deficit and hyperactivity disorders include cognitive disorders/dysfunction (including but not limited to schizophrenia, Alzheimer's disease, mild cognitive impairment, dementias), and attention deficit/hyperactivity disorder (e.g., ADD, ADHD).

Exemplified movement disorders include but are not limited to those secondary to Parkinson's disease, Huntington's disease, dyskinesias, dystonias, and tremors. Exemplified sexual dysfunctions include but are not limited to premature ejaculation and arousal disorder.

Exemplified eating disorders include but are not limited to anorexia nervosa and bulimia nervosa.

b. Pharmacological Agents

The pharmacological agents used in the present methods and compositions include the one or more active agents, described in detail below, in any pharmaceutically acceptable form, including any pharmaceutically acceptable salts, prodrugs, racemic mixtures, conformational and/or optical isomers, crystalline polymorphs and isotopic variants of the one or more pharmacological agents.

i. Selective Muscarinic Receptor $M_1$ Antagonists

The present methods treat psychological conditions, including depression, by administering to an individual in need thereof a therapeutic amount of one or more selective muscarinic receptor $M_1$ antagonists. Muscarinic antagonists are generally reviewed in Chapter 7 of *Goodman and Gilman's The Pharmacological Basis of Therapeutics*, supra, hereby incorporated herein by reference. Exemplified selective muscarinic receptor $M_1$ antagonists include pirenzepine and telenzepine, the structures of which are shown below.

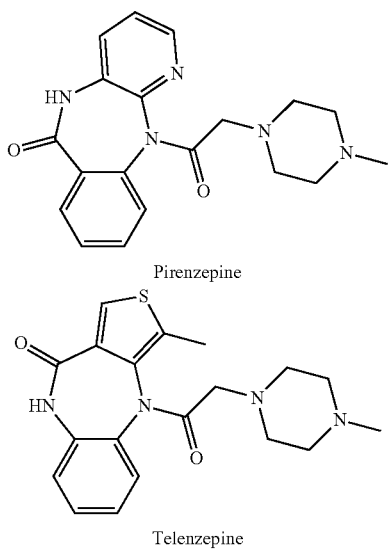

Pirenzepine

Telenzepine

Pirenzepine (5,11-Dihydro-11-[(4-methyl-1-piperazinyl)acetyl]-6H-pyrido[2,3-b][1,4]benzodiazepin-6-one) is manufactured and sold as pirenzepine dihydrochloride by several pharmaceutical companies, including Azupharma (Stuttgart, Germany), Boehringer Ingelheim (Ingelheim, Germany; sold as Gastrozepin®), Dolorgiet (Bonn, Germany). Pirenzepine can be administered in doses from about 50 mg/day to about 200 mg/day, for example, about 100-150 mg/day, or 50, 100, 150, or 200 mg/day. Alternatively, pirenzepine can be administered in doses of about 0.1 mg/kg/day to about 10 mg/kg/day, usually from about 0.7 mg/kg/day to about 5 mg/kg/day. Analogs of pirenzepine also find use in carrying out the present methods. Chemical analogs of pirenzepine are disclosed, for example, in U.S. Pat. Nos. 3,660,380; 3,743,734; and 5,324,832, the disclosures of each of which are hereby incorporated herein by reference in their entirety for all purposes.

Telenzepine (4,9-Dihydro-3-methyl-4-[(4-methyl-1-piperazinyl)acetyl]-10H-thieno[3,4-b][1,5]benzodiazepin-10-one) is commercially available from, for example, Tocris Bioscience (Ellisville, Mo.) and Sigma-Aldrich, Inc. (St. Louis, Mo.) as telenzepine dihydrochloride. Further, the synthesis of telenzepine is disclosed in U.S. Pat. No. 4,381,301, hereby incorporated herein by reference. Telenzepine can be administered in doses from about 0.5 mg per day to about 10 mg per day, for example, about 1-5 mg/day, or 0.5, 1, 2, 3, 4, 5, 6, 7, 8, 9 or 10 mg/day. Analogs of telenzepine also find use in carrying out the present methods. Chemical analogs and enantiomers of telenzepine are disclosed, for example, in U.S. Pat. Nos. 3,953,430; 4,168,269; 4,172,831; 4,381,301; 5,140,025 and 5,324,832, the disclosures of each of which are hereby incorporated herein by reference in their entirety for all purposes.

In some embodiments a racemic preparation of telenzepine containing a mixture of (+) and (−) enantiomers is administered. In some embodiments, the (+) or (−) enantiomer of telenzepine is administered. Telenzepine exists in two chirally distinct states separated by an activation barrier of 35.5 kcal/mol (Eveleigh et al., *Mol Pharmacol* (1989) 35:477-483; and Schudt et al., *Eur J Pharmacol* (1989) 165: 87-96). The (+) form of telenzepine has potent antimuscarinic activity whereas the (−) form is considerably less active. The selectivity of telenzepine appears to vary at different anatomic sites with the (+) form more effective on cortical receptors by a factor of 400 compared to the (−) isomer; on cardiac receptors the selectivity is less and the (+) form is more potent than the (−) form by a factor of 50 (Eveleigh et al., supra). The two forms interconvert slowly and with a half time of approximately 200 hours at 90 degrees (Eveleigh et al., supra). Multiple studies have affirmed that the two forms have distinct activities (Eltze, *Eur J Pharmacol* (1990) 180:161-168; Eveleigh et al., supra; Feifel et al., *Eur J Pharmacol* (1991) 195:115-123; Kilian et al., *Agents Actions Suppl* 34:131-147; Schudt et al., supra).

ii. Anti-Depressants

Antidepressant agents that are not $M_1R$-selective antagonists for use in the present invention are not limited by their mechanism of action and any class of antidepressant is applicable. For instance, tricyclic antidepressants (TCAs) and analogs thereof, serotonin reuptake inhibitors, monoamine oxidase inhibitors (MAOIs), serotonin agonists and prodrugs thereof, norepinephrine reuptake inhibitors, dopamine reuptake inhibitors, and serotonin reuptake accelerators can all be administered in combination with one or more $M_1R$-selective antagonists. Serotonin reuptake inhibitors include both selective serotonin reuptake inhibitors (SSRIs) and serotonin-norepinephrine reuptake inhibitors (SNRIs). Norepinephrine reuptake inhibitors include both the specific norepinephrine reuptake inhibitors as well as the mixed norepinephrine-dopamine reuptake inhibitors (NDRIs). Serotonin-norepinephrine-dopamine, or "triple reuptake inhibitors" also find use in the present invention. Other categories of antidepressant can also be used, for example, the tetracyclic antidepressants maprotiline or mianserin, or the agents trazodone, nefazodone, or buspirone; corticotropin releasing factor receptor 1 (CRF1) antagonists, and compounds discovered to have activity in the setting of psychosis or bipolar disorder, including amoxapine, clozapine, risperidone, olanzapine, quetiapine and aripiprazole.

Tricyclic antidepressants for use in the present invention include amineptine, amitriptyline, clomipramine, desipramine, doxepin, dothiepin, imipramine, nortriptyline, protriptyline, trimipramine, amoxapine and the muscle relaxant cyclobenzaprine. Other unlisted tricyclic antidepressants and analogs thereof can also be used.

In one embodiment, an effective amount of one or more $M_1R$-selective antagonists is co-administered with an effective amount of a selective serotonin reuptake inhibitor. Exemplary selective serotonin reuptake inhibitors include citalopram, escitalopram, fluoxetine (racemic or an optical isomer), fluvoxamine, paroxetine and sertraline (and its S-enantiomer, Zoloft®), although SSRIs not listed are applicable. In one embodiment, citalopram (or escitalopram) is co-administered with one or more $M_1R$-selective antagonists. In one embodiment, an effective amount of fluoxetine (racemic or an optical isomer) is co-administered. In one embodiment, an effective amount of fluvoxamine is co-administered. In one embodiment, an effective amount of sertraline (or its S-enantiomer, Zoloft®) is co-administered. In one embodiment, an effective amount of paroxetine is co-administered. In one embodiment, an effective amount of duloxetine is co-administered.

In one embodiment, an effective amount of one or more serotonin-norepinephrine reuptake inhibitors are co-administered with one or more $M_1R$-selective antagonist. Exemplary serotonin-norepinephrine reuptake inhibitors include milnacipran, mirtazapine, venlafaxine (racemic or an optical isomer), duloxetine, (–)1-(1-dimethylaminomethyl-5-methoxybenzo-cyclobutan-1-yl)cyclohexanol (S33005), DVS-233 (desvenlafaxine), DVS-233 SR and sibutramine, although SNRIs not listed are also of use. Although the mechanism of action of mirtazapine may differ from that of other SNRIs, owing to its apparent dual serotonergic and noradrenergic action, it is considered herein as a member of the SNRI class of antidepressants. In one embodiment, an effective amount of venlafaxine (racemic or an optical isomer) is co-administered. In one embodiment, an effective amount of desvenlafaxine is co-administered. In one embodiment, an effective amount of sibutramine is co-administered. In one embodiment, an effective amount of duloxetine is co-administered. In one embodiment, an effective amount of milnacipran is co-administered. In one embodiment, an effective amount of mirtazapine is co-administered.

In other embodiments, an effective amount of one or more selective norepinephrine reuptake inhibitors is co-administered with one or more $M_1R$-selective antagonists. Exemplary selective norepinephrine reuptake inhibitors include reboxetine and atomoxetine.

In one embodiment, an effective amount of one or more norepinephrine-dopamine reuptake inhibitors are co-administered with one or more $M_1R$-selective antagonists. Exemplary norepinephrine-dopamine reuptake inhibitors include amineptine, modafinil, GW353162 and bupropion. In the case of bupropion, metabolites are thought to be responsible for the noradrenergic reuptake blockade. In one embodiment, an effective amount of bupropion is co-administered.

In one embodiment, an effective amount of one or more triple (serotonin-norepinephrine-dopamine) reuptake inhibitors are co-administered with one or more $M_1R$-selective antagonist. Exemplary triple reuptake inhibitors include indatraline, SEP-225289, DOV 216,303 and (+)-1-(3,4-dichlorophenyl)-3-azabicyclo-[3.1.0]hexane hydrochloride (DOV 21,947).

Monoamine oxidase inhibitors for use in the present invention include befloxatone, brofaromine, deprenyl, isocarboxazid, moclobemide, pargyline, phenelzine, selegiline and tranylcypromine, together with their sustained delivery and transdermal delivery forms.

Antidepressants that can be co-administered with an $M_1R$-selective antagonist include maprotiline, tianeptine, nefazodone and trazodone.

Appropriate dosages for antidepressants will depend on the chosen route of administration and formulation of the composition, among other factors. For instance, tricyclic antidepressants are administered at a dose of about 25 to about 600 mg/day, and usually at a dose of about 75 to about 300 mg/day.

Serotonin-reuptake inhibitors are administered at a dose of about 5 to about 400 mg/day, and usually administered at about 20 to about 250 mg/day. In particular, in practicing the present methods, venlafaxine (racemic or an optical isomer) can be administered at about 9 mg to about 225 mg per dose, and is usually administered at about 37.5 mg, 75 mg, 150 mg or 225 mg per dose. Venlafaxine is typically administered at about 25-550 mg/day and usually at about 37.5-375 mg/day, more typically about 75-225 mg/day, and most typically at about 37.5, 75, 150, 225, or 300 mg/day. As appropriate for an individual patient, daily venlafaxine dosages can be divided and administered one time, two times, three times, four or more times a day. Desvenlafaxine can be administered at a dose of about 50-600 mg/day, for example, about 50, 100, 200, 400 or 600 mg/day. Sertraline (or its S-enantiomer, Zoloft®) can be administered in doses ranging from about 50-200 mg/day, usually about 100-150 mg/day. Fluoxetine (racemic or an optical isomer) can be administered in doses ranging from about 5-50 mg/day, usually about 20-40 mg/day. Fluvoxamine can be administered in doses ranging from about 50-300 mg/day, usually about 100-200 mg/day. Paroxetine can be administered in doses ranging from about 10-50 mg/day, usually about 20-40 mg/day.

In carrying out the present methods, citalopram (or escitalopram) can be administered at about 5-60 mg/day, and preferably at about 10, 20 or 30 mg/day. Usually, citalopram is administered once a day, for instance in the morning or in the evening. However, some patients are given dosages of citalopram two or more times a day. Mirtazapine can be administered at a dose of about 5-100 mg/day, for example, about 7.5, 15, 30, 45 or 90 mg/day. Milnacipran can be administered at a dose of about 25-200 mg/day, for example, about 25, 50, 100, 150 or 200 mg/day.

Atypical antidepressants, including bupropion, nefazodone and trazodone are administered at a dose of about 50-600 mg/day, and usually at about 150-400 mg/day. Bupropion can be administered at a dose of about 25-300 mg/day, for example, about 25, 50, 100, 150, 200, 300 mg/day. Monoamine oxidase inhibitors are typically administered at a dose of about 5-90 mg/day, and usually at about 10-60 mg/day.

iii. Combinations of Pharmacological Agents

In some embodiments, the one or more $M_1R$-selective antagonists are co-administered or co-formulated with and one or more antidepressants that are not a $M_1R$-selective antagonist. The $M_1R$-selective antagonists and antidepressants are as described above.

In some embodiments, the one or more $M_1R$-selective antagonists are co-administered or co-formulated with and one or more 5-HT2c receptor agonists. Exemplified 5-HT2c receptor agonists include 1-(m-chlorophenyl)piperazine (m-CPP), mirtazapine, APD-356 (lorcaserin), SCA-136 (vabicaserin), ORG-12962, ORG-37684, ORG-36262, ORG-8484, Ro-60-175, Ro-60-0332, VER-3323, VER-5593, VER-5384, VER-8775, LY-448100, WAY-161503, WAY-470, WAY-163909, MK-212, BVT.933, YM-348, IL-639, IK-264, ATH-88651, ATHX-105 and the like (see, e.g., Nilsson B M, J. Med. Chem. 2006, 49:4023-4034).

In some embodiments, the one or more $M_1R$-selective antagonists are co-administered or co-formulated with m-CPP. In some embodiments, the one or more $M_1R$-selective antagonists are co-administered or co-formulated with mirtazapine. In some embodiments, the one or more $M_1R$-selective antagonists are co-administered or co-formulated with lorcaserin. In some embodiments, the one or more $M_1R$-selective antagonists are co-administered or co-formulated with Ro-60-175. In some embodiments, the one or more $M_1R$-selective antagonists are co-administered or co-formulated with Ro-60-0332.

In some embodiments, a combination of one or more $M_1R$-selective antagonists, one or more antidepressants that are not a $M_1R$-selective antagonist, and one or more 5-HT2c receptor agonists is administered.

iv. Isomers

All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers of the therapeutic agents are within the scope of the present invention.

v. Isotopes

The present invention also includes isotopically-labeled variants of the therapeutic agents, wherein one or more atoms are replaced by one or more atoms having specific atomic mass or mass numbers. Isotopically-labeled variants of the therapeutic agents and prodrugs thereof, as well as isotopically-labeled, pharmaceutically acceptable salts of the therapeutic agents and prodrugs thereof, are within the scope of the present invention. In certain circumstances substitution with heavier isotopes, such as deuterium ($^2H$), can provide increased metabolic stability, which offers therapeutic advantages such as increased in vivo half-life or reduced dosage requirements. Isotopically-labeled variants of the therapeutic agents of this invention and prodrugs thereof can generally be prepared according to methods known to those skilled in the art by substituting an isotopically-labeled reagent for a non-isotopically labeled reagent.

c. Administration i. Duration of Administration

Usually, the one or more $M_1R$-selective antagonists are administered to the individual over an extended period of time. The methods can be carried out for at least 20 days, in some embodiments for at least 40, 60, 80 or 100 days, and in some embodiments for at least 150, 200, 250, 300, 350 days, 1 year or longer. Certain individuals receive the present treatment methods for longer than a year, for example, at least 400, 450, 500, 550, 600, 650, 700, 800, 900, 1000 days. However, individuals can be successfully treated with the present methods for 2 years, 3 years, 4 years or longer.

ii. Scheduling

Generally, in practicing the present methods, effective amounts of one or more $M_1R$-selective antagonists co-administered with one or more antidepressants can be administered together or separately, simultaneously or at different times. The $M_1R$-selective antagonists and antidepressants independently can be administered once, twice, three, four times daily or more or less often, as needed. Preferably, the one or more $M_1R$-selective antagonists and the one or more antidepressants are administered once daily. Preferably, the one or more $M_1R$-selective antagonists and the one or more antidepressants are administered at the same time or times, for instance as an admixture. The one or more $M_1R$-selective antagonists and one or more antidepressants can be administered in a sustained-release formulation.

For certain patients, the methods are carried out concurrently administering the one or more $M_1R$-selective antagonists and then the one or more antidepressants from the initiation of treatment. For certain patients, the methods are carried out by first administering the one or more $M_1R$-selective antagonists, and then subsequently co-administering the one or more antidepressants. The patient initially can be given the one or more $M_1R$-selective antagonists alone for as long as 3 days, 5 days, 7 days, 10 days, 14 days, 20 days, or 30 days before commencing administration of one or more antidepressants.

The one or more $M_1R$-selective antagonists can be administered prophylactically to prevent symptoms of a psychological conditions in a subject at risk, or therapeutically to ameliorate symptoms of the psychological condition for a sustained period of time.

iii. Routes of Administration

As such, administration of one or more $M_1R$-selective antagonists, alone or in combination with one or more antidepressants, can be achieved in various ways, including oral, buccal, parenteral, including intravenous, intradermal, subcutaneous, intramuscular, transdermal, transmucosal, intranasal, etc., administration. The one or more $M_1R$-selective antagonists can be administered by the same or different route of administration when co-administered with one or more antidepressants.

In some embodiments, one or more $M_1R$-selective antagonists, alone or in combination, can be administered in a local rather than systemic manner, for example, in a depot or sustained release formulation.

iv. Methods of Determining Appropriate Dosages

Administered dosages for $M_1R$-selective antagonists and antidepressants are in accordance with dosages and scheduling regimens practiced by those of skill in the art. General guidance for appropriate dosages of all pharmacological agents used in the present methods is provided in *Goodman and Gilman's The Pharmacological Basis of Therapeutics*, 11th Edition, 2006, supra, and in a Physicians' Desk Reference (PDR), for example, in the $59^{th}$ (2005) or $60^{th}$ (2006) Eds., Thomson PDR, each of which is hereby incorporated herein by reference. Published dosages for $M_1R$-selective antagonists are for indications distinct from treatments to ameliorate depression or other psychological conditions. In the compositions and methods of the present invention, efficacious dosages of $M_1R$-selective antagonists and antidepressants for practicing the present invention can be equal to or less than (e.g., about 25, 50, 75 or 100%) the dosages published for other indications.

The appropriate dosage of one or more $M_1R$-selective antagonists and antidepressants will vary according to several factors, including the chosen route of administration, the formulation of the composition, patient response, the severity of the condition, the subject's weight, and the judgment of the prescribing physician. The dosage can be increased or decreased over time, as required by an individual patient. Usually, a patient initially is given a low dose, which is then increased to an efficacious dosage tolerable to the patient.

Determination of an effective amount is well within the capability of those skilled in the art, especially in light of the detailed disclosure provided herein. Generally, an efficacious or effective amount of a combination of one or more $M_1R$-selective antagonists and one or more antidepressants is determined by first administering a low dose or small amount of an $M_1R$-selective antagonist alone, and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics,* 11th Edition, 2006, supra; in a Physicians' Desk Reference (PDR), supra; in *Remington: The Science and Practice of Pharmacy,* 21$^{st}$ Ed., 2006, supra; and in *Martindale: The Complete Drug Reference,* Sweetman, 2005, London: Pharmaceutical Press., and in Martindale, *Martindale: The Extra Pharmacopoeia,* 31st Edition., 1996, Amer Pharmaceutical Assn, each of which are hereby incorporated herein by reference.

Dosage amount and interval can be adjusted individually to provide plasma levels of the active compounds which are sufficient to maintain therapeutic effect. Preferably, therapeutically effective serum levels will be achieved by administering single daily doses, but efficacious multiple daily dose schedules are included in the invention. In cases of local administration or selective uptake, the effective local concentration of the drug may not be related to plasma concentration. One having skill in the art will be able to optimize therapeutically effective local dosages without undue experimentation.

3. Pharmaceutical Compositions

The present invention further provides pharmaceutical compositions comprising a mixture of a therapeutically effective amount of one or more $M_1R$-selective antagonists and one or more antidepressants. In some embodiments, the $M_1R$-selective antagonists are selected from the group consisting of telenzepine, pirenzepine and mixtures thereof.

In certain embodiments, the pharmaceutical compositions comprise one or more antidepressants that are a selective serotonin reuptake inhibitor (SSRI), a serotonin-norepinephrine reuptake inhibitor (SNRI), a norepinephrine reuptake inhibitor, a dopamine reuptake inhibitor, a norepinephrine-dopamine reuptake inhibitor (NDRI), a serotonin-norepinephrine-dopamine reuptake inhibitor, a serotonin reuptake accelerator, a serotonin agonist and prodrugs thereof. In one embodiment, the pharmaceutical composition comprises one or more antidepressants selected from the group consisting of venlafaxine (racemic or an optical isomer), duloxetine, fluoxetine (racemic or an optical isomer), citalopram, escitalopram, fluvoxamine, paroxetine, S33005, DVS-233 (desvenlafaxine), DVS-233 SR, bupropion, GW353162, sibutramine, atomoxetine and sertraline (or its S-enantiomer, Zoloft®).

In one embodiment, the pharmaceutical composition comprises therapeutically effective amounts of telenzepine or pirenzepine and an SSRI. In one embodiment, the pharmaceutical composition comprises therapeutically effective amounts of telenzepine or pirenzepine and citalopram (or escitalopram). In one embodiment, the pharmaceutical composition comprises therapeutically effective amounts of telenzepine or pirenzepine and sertraline (or its S-enantiomer, Zoloft®). In one embodiment, the pharmaceutical composition comprises therapeutically effective amounts of telenzepine or pirenzepine and fluoxetine (racemic or an optical isomer). In one embodiment, the pharmaceutical composition comprises therapeutically effective amounts of telenzepine or pirenzepine and fluvoxamine. In one embodiment, the pharmaceutical composition comprises therapeutically effective amounts of telenzepine or pirenzepine and paroxetine.

In one embodiment, the pharmaceutical composition comprises therapeutically effective amounts of telenzepine or pirenzepine and an SNRI. In one embodiment, the pharmaceutical composition comprises therapeutically effective amounts of telenzepine or pirenzepine and venlafaxine (racemic or an optical isomer). In one embodiment, the pharmaceutical composition comprises therapeutically effective amounts of telenzepine or pirenzepine and desvenlafaxine. In one embodiment, the pharmaceutical composition comprises therapeutically effective amounts of telenzepine or pirenzepine and duloxetine. In one embodiment, the pharmaceutical composition comprises therapeutically effective amounts of telenzepine or pirenzepine and milnacipran. In one embodiment, the pharmaceutical composition comprises therapeutically effective amounts of telenzepine or pirenzepine and mirtazapine.

In one embodiment, the pharmaceutical composition comprises therapeutically effective amounts of telenzepine or pirenzepine and bupropion.

A combination of one or more $M_1R$-selective antagonists and one or more antidepressants can be administered to a subject, e.g., a human patient, a domestic animal such as a cat or a dog, independently or together in the form of their pharmaceutically acceptable salts, or in the form of a pharmaceutical composition where the compounds are mixed with suitable carriers or excipient(s) in a therapeutically effective amount, e.g., at doses effective to effect desired result of reducing the symptoms of the psychological condition.

An $M_1R$-selective antagonist-antidepressant combination of this invention can be incorporated into a variety of formulations for therapeutic administration. More particularly, a combination of the present invention can be formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols.

Suitable formulations for use in the present invention are found in, for example, in *Remington: The Science and Practice of Pharmacy,* 21$^{st}$ Ed., 2006, supra; *Martindale: The Complete Drug Reference,* Sweetman, 2005, London: Pharmaceutical Press; Niazi, *Handbook of Pharmaceutical Manufacturing Formulations,* 2004, CRC Press; and Gibson, *Pharmaceutical Preformulation and Formulation: A Practical Guide from Candidate Drug Selection to Commercial Dosage Form,* 2001, Interpharm Press, which are hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In one embodiment, an $M_1R$-selective antagonist-antidepressant combination is prepared for delivery in a sustained-release, controlled release, extended-release, timed-release or delayed-release formulation, for example, in semi-permeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering an $M_1R$-selective antagonist-antidepressant combination of the present invention include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

For oral administration, an $M_1R$-selective antagonist-antidepressant combination can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compounds can be formulated for parenteral administration by injection, e.g., by bolus injection or continuous infusion. For injection, an $M_1R$-selective antagonist-antidepressant combination can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, a combination of the invention can be formulated in aqueous solutions, preferably in physiologically compatible buffers such as Hanks's solution, Ringer's solution, or physiological saline buffer. Formulations for injection can be presented in unit dosage faun, e.g., in ampules or in multidose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. For topical administration, the agents are formulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use in the present invention include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

For buccal administration, the compositions can take the form of tablets or lozenges formulated in a conventional manner.

In addition to the formulations described previously, an $M_1R$-selective antagonist-antidepressant combination of the present invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

4. Kits

The pharmaceutical compositions of the present invention can be provided in a kit. In certain embodiments, a kit of the present invention comprises one or more $M_1R$-selective antagonists and one or more antidepressants in separate formulations. In certain embodiments, the kits comprise one or more $M_1R$-selective antagonists and one or more antidepressants within the same formulation. In certain embodiments, the kits provide the one or more $M_1R$-selective antagonists and one or more antidepressants independently in uniform dosage formulations throughout the course of treatment. In certain embodiments, the kits provide the one or more $M_1R$-selective antagonists and one or more antidepressants independently in graduated dosages over the course of treatment, either increasing or decreasing, but usually increasing to an efficacious dosage level, according to the requirements of an individual.

In one embodiment, the kits comprise one or more pharmaceutical compositions comprising one or more $M_1R$-selective antagonists selected from the group consisting of telenzepine and pirenzepine.

In certain embodiments, the kits comprise one or more antidepressants selected from the group consisting of a selective serotonin reuptake inhibitor (SSRI), a serotonin-norepinephrine reuptake inhibitor (SNRI), a norepinephrine reuptake inhibitor, a dopamine reuptake inhibitor, a norepinephrine-dopamine reuptake inhibitor (NDRI), a serotonin-norepinephrine-dopamine reuptake inhibitor, and mixtures thereof. In one embodiment, the kits comprise one or more pharmaceutical compositions comprising one or more antidepressants selected from the group consisting of venlafaxine (racemic or an optical isomer), fluoxetine (racemic or an optical isomer), duloxetine, paroxetine, citalopram, escitalopram, fluvoxamine, S33005, DVS-233 (desvenlafaxine), DVS-233 SR, bupropion, GW353162, sibutramine, atomoxetine and sertraline (or its S-enantiomer, Zoloft®).

In one embodiment, the kit comprises therapeutically effective amounts of telenzepine or pirenzepine and an SSRI. In one embodiment, the kit comprises therapeutically effective amounts of telenzepine or pirenzepine and citalopram (or escitalopram). In one embodiment, the kit comprises therapeutically effective amounts of telenzepine or pirenzepine and sertraline (or its S-enantiomer, Zoloft®). In one embodiment, the kit comprises therapeutically effective amounts of telenzepine or pirenzepine and fluoxetine (racemic or an optical isomer). In one embodiment, the kit comprises therapeutically effective amounts of telenzepine or pirenzepine and fluvoxamine. In one embodiment, the kit comprises therapeutically effective amounts of telenzepine or pirenzepine and paroxetine.

In one embodiment, the kit comprises therapeutically effective amounts of telenzepine or pirenzepine and an SNRI. In one embodiment, the kit comprises therapeutically effective amounts of telenzepine or pirenzepine and venlafaxine (racemic or an optical isomer). In one embodiment, the kit comprises therapeutically effective amounts of telenzepine or pirenzepine and desvenlafaxine. In one embodiment, the kit comprises therapeutically effective amounts of telenzepine or pirenzepine and duloxetine. In one embodiment, the kit comprises therapeutically effective amounts of telenzepine or pirenzepine and milnacipran. In one embodiment, the kit comprises therapeutically effective amounts of telenzepine or pirenzepine and mirtazapine.

In one embodiment, the kit comprises therapeutically effective amounts of telenzepine or pirenzepine and bupropion.

EXAMPLES

The following examples are offered to illustrate, but not to limit the claimed invention.

Example 1

Antidepressant Effects: The tail suspension methodology was used to assess compounds for their antidepressant effects. The methodology was adapted from the original description by Stem et al. (Stem L, et al., *Psychopharmacol* 85:367-70, 1985; Stem L, et al., *Prog Neuro-Psychopharmacol & Biol Psychiat* 11:659-71, 1987) and later modifications by Crowley et al. (Crowley J J, et al., *Pharmacol Biochem Beh* 78(2):269-74, 2004). Seven- to eight-week-old (25-35 grams) male, CD-1 mice were housed for one week prior to testing. Mice (n=8-10 per dose group) were dosed intraperitoneally (ip) or orally (po) with the compound under investigation, and returned to their home cage for the appropriate pretreatment interval (45-60 min). Using tape, the mice were then suspended by the tail from a strain gauge. Activity over the next 6 minutes was scored by computer as either: 1) Immobility, 2) Escape Behavior or 3) Major Escape Behavior, based on the intensity of movements registered by the strain gauge. Total Immobility was calculated and expressed in seconds. In this assay, vehicle-treated mice typically spend approximately 30% of the session immobile, while pretreatment with antidepressants significantly shortens this cumulative immobility. Treatment effects are presented in Table 1 and FIGS. 1-6 as both raw Time Spent Immobile (in seconds±SEM [standard error of the mean]) and as % Reduction in Immobility=[1−(Treatment Immobility/Vehicle Immobility)]×100%. Similar superscripts in the Dose column of Table 1 denote values derived from the same experiment (to facilitate comparisons between individual treatments and co-administrations). Statistical analyses were performed using a 1-way ANOVA (analysis of variance) followed by a Bonferroni multiple comparison test with the overall alpha set at 0.05. In Table 1, asterisks (*) denote significant effects compared to vehicle-treated mice, while letters (a or b) denote significant effects compared to mice treated with a single compound ("a" for significance from antidepressant and "b" for significance from telenzepine). In Table 1, the symbol denotes p<0.05, two symbols denote p<0.01 and three symbols denote p<0.001). The symbols used for denoting statistical significance may be different in the corresponding figures.

TABLE 1

| Compound | Dose (mg/kg) | Vehicle Immobility Time (sec) | Treatment Immobility Time (sec) | Reduction in Immobility | p Values |
|---|---|---|---|---|---|
| Telenzepine | 5 (ip)$^a$ | 115 ± 16 | 80 ± 14 | 30% | n.s. |
|  | 5 (ip)$^b$ | 114 ± 19 | 90 ± 18 | 21% | n.s. |
|  | 5 (ip)$^d$ | 125 ± 14 | 159 ± 23 | −27% | n.s. |
|  | 10 (ip)$^c$ | 97 ± 20 | 64 ± 15 | 34% | n.s. |
|  | 25 (ip)$^d$ | 125 ± 14 | 84 ± 07 | 33% | * |
|  | 50 (ip)$^d$ | 125 ± 14 | 61 ± 11 | 51% | *** |
|  | 60 (po)$^e$ | 130 ± 21 | 71 ± 15 | 45% | * |
|  | 80 (po)$^e$ | 130 ± 21 | 82 ± 18 | 37% | * |
|  | 100 (po)$^e$ | 130 ± 21 | 59 ± 10 | 55% | ** |
| Pirenzepine | 5 (ip)$^f$ | 123 ± 20 | 137 ± 15 | −11% | n.s. |
|  | 25 (ip)$^f$ | 123 ± 20 | 90 ± 17 | 27% | n.s. |
|  | 50 (ip)$^f$ | 123 ± 20 | 76 ± 12 | 38% | * |
| Fluoxetine | 4 (ip)$^c$ | 97 ± 20 | 97 ± 11 | 0% | n.s. |
|  | 4 (ip)$^g$ | 146 ± 18 | 81 ± 16 | 45% | ** |
|  | 20 (ip)$^g$ | 146 ± 18 | 82 ± 16 | 45% | ** |
|  | 40 (ip)$^g$ | 146 ± 18 | 53 ± 14 | 64% | *** |
| Sertraline | 1 (ip)$^a$ | 115 ± 16 | 87 ± 14 | 24% | n.s. |
|  | 5 (ip)$^h$ | 121 ± 17 | 63 ± 08 | 48% | ** |
|  | 20 (ip)$^h$ | 121 ± 17 | 50 ± 16 | 59% | ** |
|  | 40 (ip)$^h$ | 121 ± 17 | 44 ± 15 | 64% | *** |
| Venlafaxine | 3 (ip)$^i$ | 112 ± 15 | 103 ± 21 | 8% | n.s. |
|  | 10 (ip)$^i$ | 112 ± 15 | 116 ± 20 | −4% | n.s. |
|  | 10 (ip)$^b$ | 114 ± 19 | 103 ± 15 | 10% | n.s. |
|  | 30 (ip)$^i$ | 112 ± 15 | 31 ± 09 | 72% | *** |
| Telenzepine + Fluoxetine | 10 + 4$^c$ (ip) | 97 ± 20 | 45 ± 09 | 54% | ** |
| Telenzepine + Sertraline | 5 + 1$^a$ (ip) | 115 ± 16 | 66 ± 12 | 43% | *** |
| Telenzepine + Venlafaxine | 5 + 10$^b$ (ip) | 114 ± 19 | 29 ± 09 | 75% | **, aa, b |

Note on Effects:

As summarized in Table 1, systemic administration of pirenzepine alone at 50 mg/kg ip (FIG. 1) or telenzepine alone at 25 mg/kg ip (FIG. 2) or 60 mg/kg po (FIG. 3) produces significant reduction in immobility.

Figure 4:
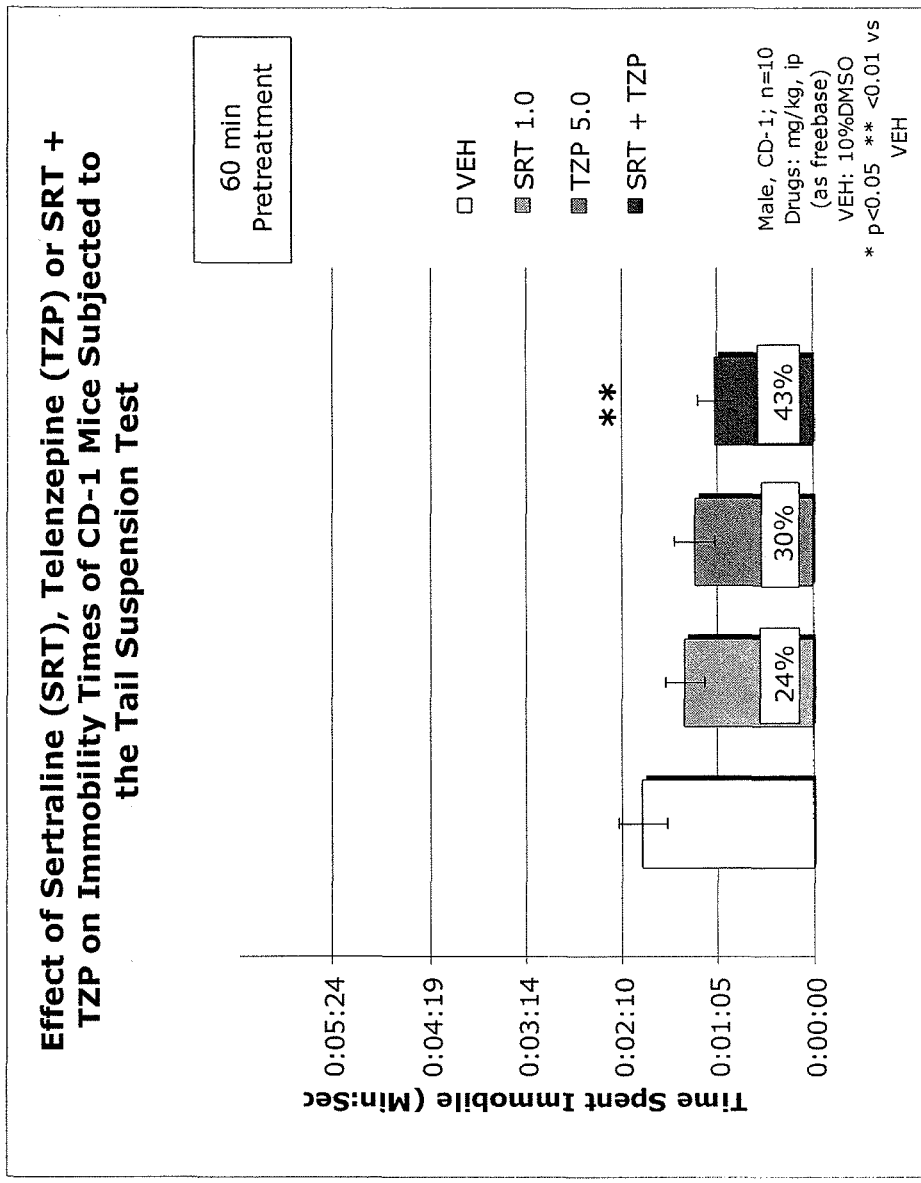
FIG. 4 illustrates the effect of combined administration of telenzepine (TZP) and sertraline (SRT) on immobility times of CD-1 mice subjected to the tail suspension test. Male CD-1 mice (n=10 per group) were administered intraperitoneally as free base telenzepine alone (5.0 mg/kg), sertraline alone (1.0 mg/kg), or co-administered telenzepine (5.0 mg/kg) and sertraline (1.0 mg/kg) as described in the Examples below. Control mice (VEH) were administered 10% DMSO. ** indicates p<0.01 vs. VEH.
Figure 5:
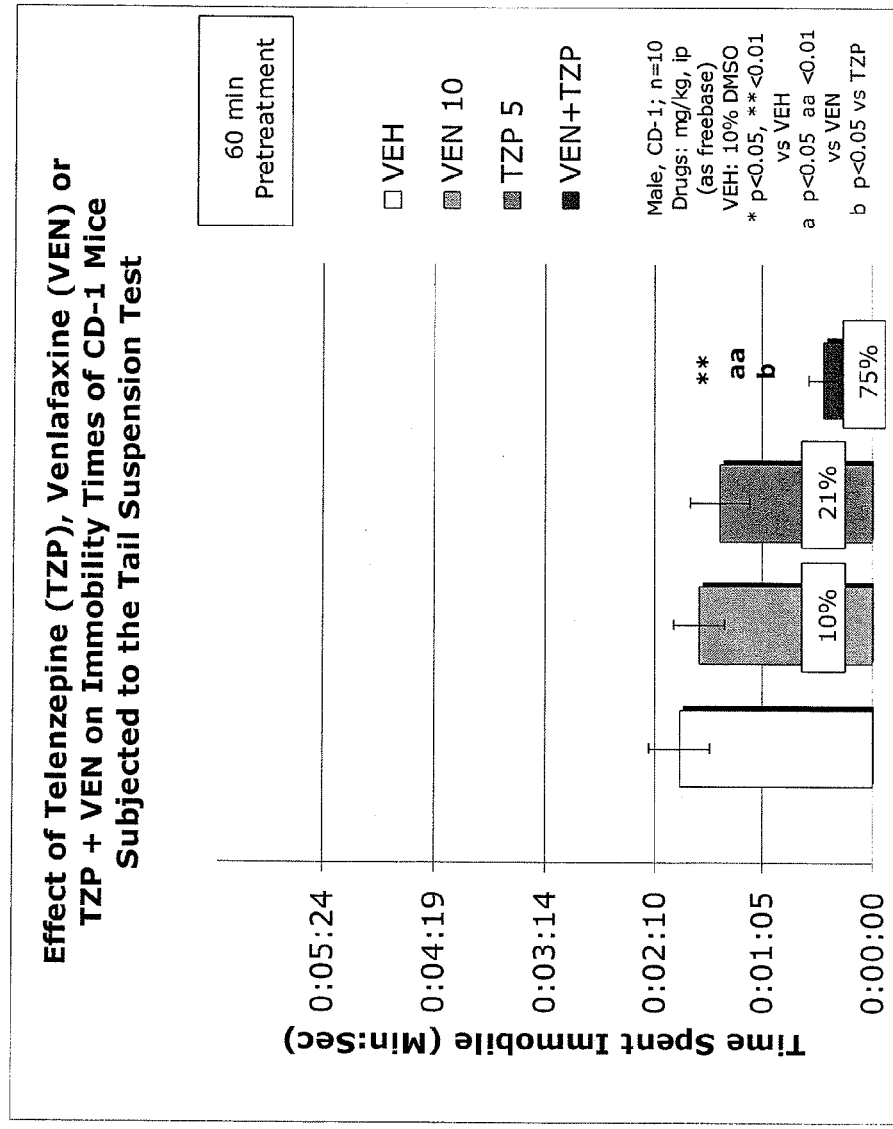
FIG. 5 illustrates the effect of combined administration of telenzepine (TZP) and venlafaxine (VEN) on immobility times of CD-1 mice subjected to the tail suspension test. Male CD-1 mice (n=10 per group) were administered intraperitoneally as free base telenzepine alone (5.0 mg/kg), venlafaxine alone (10 mg/kg), or co-administered telenzepine (5.0 mg/kg) and venlafaxine (10 mg/kg) as described in the Examples below. Control mice (VEH) were administered 10% DMSO. * indicates p<0.05 vs. VEH. ** indicates p<0.01 vs. VEH. "aa" indicates p<0.01 vs. VEN. "b" indicates p<0.05 vs. TZP.
Figure 6:
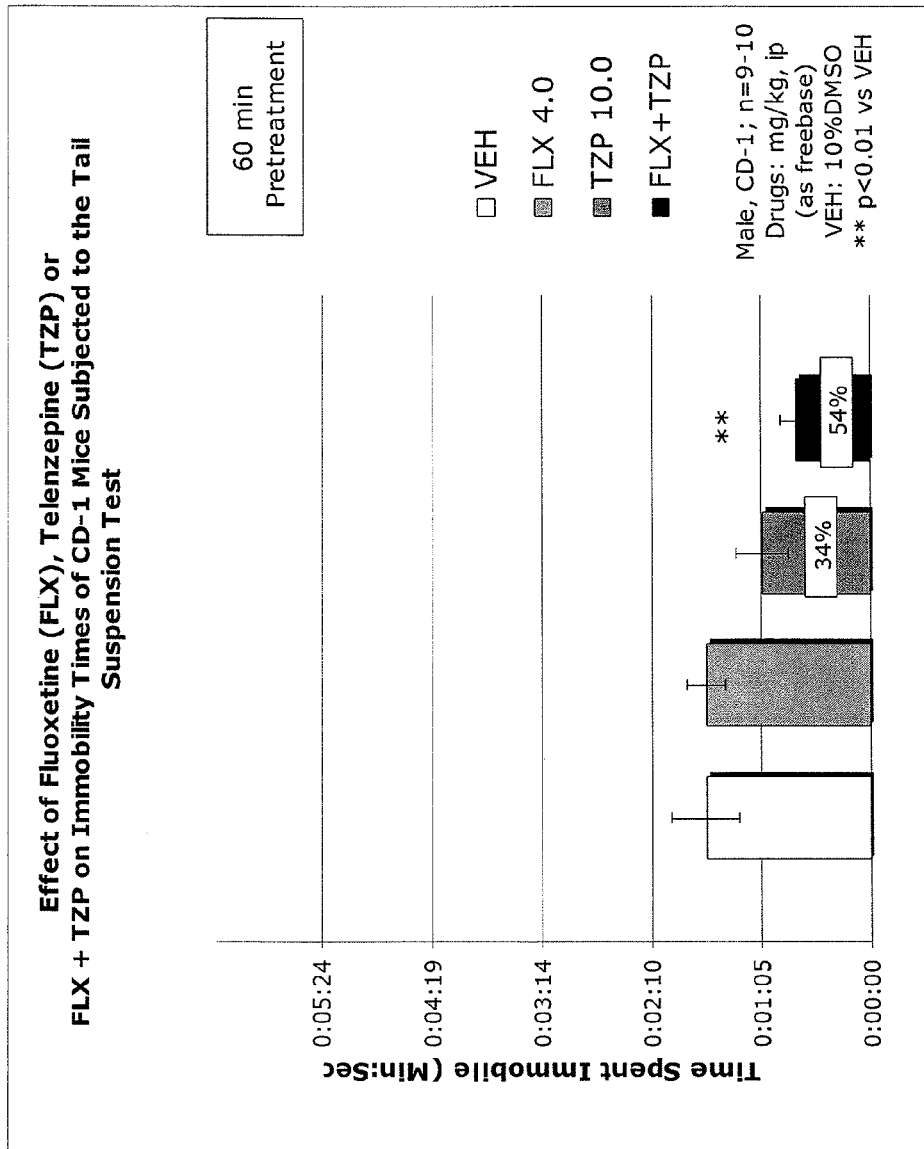
FIG. 6 illustrates the effect of combined administration of telenzepine (TZP) and fluoxetine (FLX) on immobility times of CD-1 mice subjected to the tail suspension test. Male CD-1 mice (n=10 per group) were administered intraperitoneally as free base telenzepine alone (10 mg/kg), fluoxetine alone (4 mg/kg), or co-administered telenzepine (10 mg/kg) and fluoxetine (4 mg/kg) as described in the Examples below. Control mice (VEH) were administered 10% DMSO. ** indicates p<0.01 vs. VEH.

When telenzepine is co-administered with an antidepressant, all three combinations tested display the principle that subactive doses of each compound can be combined to produce significant effects that generally appear synergistic. The telenzepine+venlafaxine combination demonstrated the greatest efficacy of the tested combinations. Co-administration of telenzepine and venlafaxine produces a significant (p<0.01) reduction of 75%, well beyond the 31% reduction that would be expected from mere additivity (FIG. 5). Likewise, co-administration of 10 mg/kg telenzepine+4 mg/kg fluoxetine results in a significant (p<0.01) reduction in immobility of 54%, an effect greater than expected from the contributions of the individual compounds (FIG. 6). Co-administration of telenzepine and sertraline produces a significant 43% reduction in immobility (FIG. 4).

The combinations of selective $M_1R$-antagonists and antidepressants demonstrate that the "effective dose" of the antidepressant compound can be lowered dramatically by co-administering an $M_1R$-antagonists (e.g., telenzepine). The venlafaxine dose can be lowered 3 fold (to 10 mg/kg) and still retain efficacy by co-administering 5 mg/kg telenzepine. Compare the 72% reduction in immobility when 30 mg/kg venlafaxine is administered alone to the 75% reduction in immobility when 10 mg/kg venlafaxine is co-administered with 5 mg/kg telenzepine. Similarly, the sertraline dose can be lowered 5-fold (to 1 mg/kg) and still retain efficacy by co-administering 5 mg/kg TZP. Compare the 48% reduction in immobility when 5 mg/kg sertraline is administered alone to the 43% reduction in immobility when 1 mg/kg sertraline is co-administered with 5 mg/kg telenzepine. It is estimated that the effective fluoxetine dose can be lowered approximately 7-fold (to 4 mg/kg) by co-administering 10 mg/kg TZP.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for treating depression, the method comprising systemically administering to an individual in need thereof telenzepine at a dose of about 0.5 mg per day to about 10 mg per day and an antidepressant selected from the group consisting of sertraline, fluoxetine, and venlafaxine.

2. The method of claim 1, wherein the telenzepine is administered at a dose of about 1 mg per day to about 5 mg per day.

3. The method of claim 1, wherein the antidepressant is sertraline.

4. The method of claim 3, wherein the sertraline is administered at a dose of about 50 mg per day to about 200 mg per day.

5. The method of claim 1, wherein the antidepressant is fluoxetine.

6. The method of claim 5, wherein the fluoxetine is administered at a dose of about 5 mg per day to about 50 mg per day.

7. The method of claim 1, wherein the antidepressant is venlafaxine.

8. The method of claim 7, wherein the venlafaxine is administered at a dose of about 25 mg per day to about 550 mg per day.

9. The method of claim 1, wherein the telenzepine and the antidepressant are administered concurrently.

10. The method of claim 1, wherein the telenzepine and the antidepressant are administered sequentially.

11. The method of claim 1, wherein the telenzepine is administered in a sustained-release formulation.

12. The method of claim 1, wherein the telenzepine and the antidepressant are administered as an admixture.

13. The method of claim 1, wherein the telenzepine and the antidepressant are administered for at least 60 days.

* * * * *